(12) United States Patent
Looker et al.

(10) Patent No.: US 7,264,921 B2
(45) Date of Patent: Sep. 4, 2007

(54) NO SYNTHASE ASSAY PARTICLES AND METHOD

(75) Inventors: Michael Roger Looker, Whitchurch Cardiff (GB); David Williams, Whitchurch Cardiff (GB)

(73) Assignee: GE Healthcare UK Limited, Amersham (GB)

( * ) Notice: Subject to any disclaimer, the term of this patent is extended or adjusted under 35 U.S.C. 154(b) by 277 days.

(21) Appl. No.: 10/473,240

(22) PCT Filed: Mar. 11, 2002

(86) PCT No.: PCT/GB02/01086

§ 371 (c)(1),
(2), (4) Date: Feb. 24, 2004

(87) PCT Pub. No.: WO02/077650

PCT Pub. Date: Oct. 3, 2002

(65) Prior Publication Data

US 2004/0152147 A1     Aug. 5, 2004

(30) Foreign Application Priority Data

Mar. 27, 2001   (GB)   ................. 0107563.9

(51) Int. Cl.
*C12Q 1/00*   (2006.01)
*G01N 33/58*   (2006.01)
(52) U.S. Cl. .......................................................... 435/4
(58) Field of Classification Search .................. None
See application file for complete search history.

(56) References Cited

U.S. PATENT DOCUMENTS

| 4,278,651 A | 7/1981 | Hales |
| 4,568,649 A | 2/1986 | Bertoglio-Matte |
| 6,103,379 A | 8/2000 | Margel et al. |
| 6,150,500 A * | 11/2000 | Salerno ...................... 530/300 |

FOREIGN PATENT DOCUMENTS

| EP | 0 556 0005 | 8/1993 |
| JP | 6299146 | 10/1994 |
| WO | WO91/08489 | 6/1991 |
| WO | WO96/11054 | 4/1996 |
| WO | WO99/09415 | 2/1999 |
| WO | WO00/69986 | 11/2000 |

OTHER PUBLICATIONS

Bosworth, et al. "Scintillation Proximity Assay" Nature, MacMillan Journals Ltd., London, Great Britain vol. 341, Sep. 1989, pp. 167-168.
Cook, N. D. "Scintillation Proximity Assay: A Versatile High-Throughput Screening Technology" Drug Discovery Today, Elsevier Science Ltd., Great Britain vol. 1, No. 7, Jul. 1996, pp. 287-294.
"Methods in Enzymology" vol. 301, 1999, pp. 114-125.
Alderton, W., et al. "Nitroarginine and tetrahydrobiopterin binding to the haem domain of neuronal nitric oxide synthase using a scintillation proximity assay" Biochemical Journal, vol. 332, No. 1, May 15, 1998, pp. 195-201.
Macarron, R., et al. "A homogenous method to measure aminoacyl-tRNA synthetase aminoacylation activity using scintillation proximity assay technology" Analytical Biochemistry, vol. 284, No. 2, Sep. 10, 2000, pp. 183-190.
Woodbury, C. P., et al. "Methods of Screening Combinatorial Libraries Using Immobilized or Restrained Receptors" Journal of Chromatography B: Biomedical Sciences and Applications, Elsevier Science Publishers, NL, vol. 725, No. 1, Apr. 2, 1999, pp. 113-137.

* cited by examiner

*Primary Examiner*—Christopher R. Tate
*Assistant Examiner*—Amanda P. Wood
(74) *Attorney, Agent, or Firm*—Yonggang Ji

(57) ABSTRACT

The invention relates to particles for use in a scintillation proximity assays. In particular, the invention relates to particles for use in a scintillation proximity assay for detecting nitric oxide synthase activity in a sample. The invention also relates to a method of measuring nitric oxide synthase activity in a sample using these particles in a scintillation proximity assay. The invention further relates to methods using these particles to detect the presence of modulators of nitric oxide synthase activity.

6 Claims, 13 Drawing Sheets

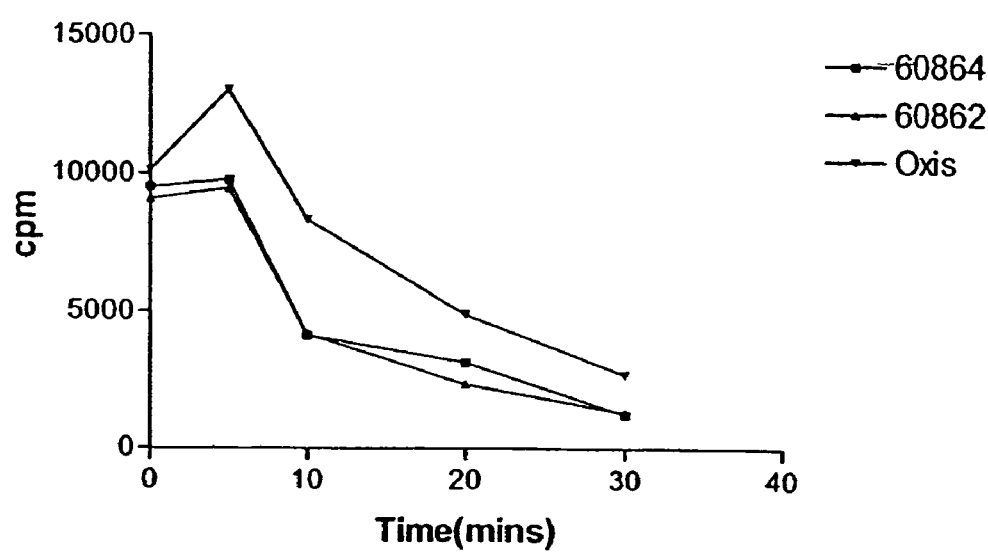
Figure 1: Activity of iNOS enzymes from different sources

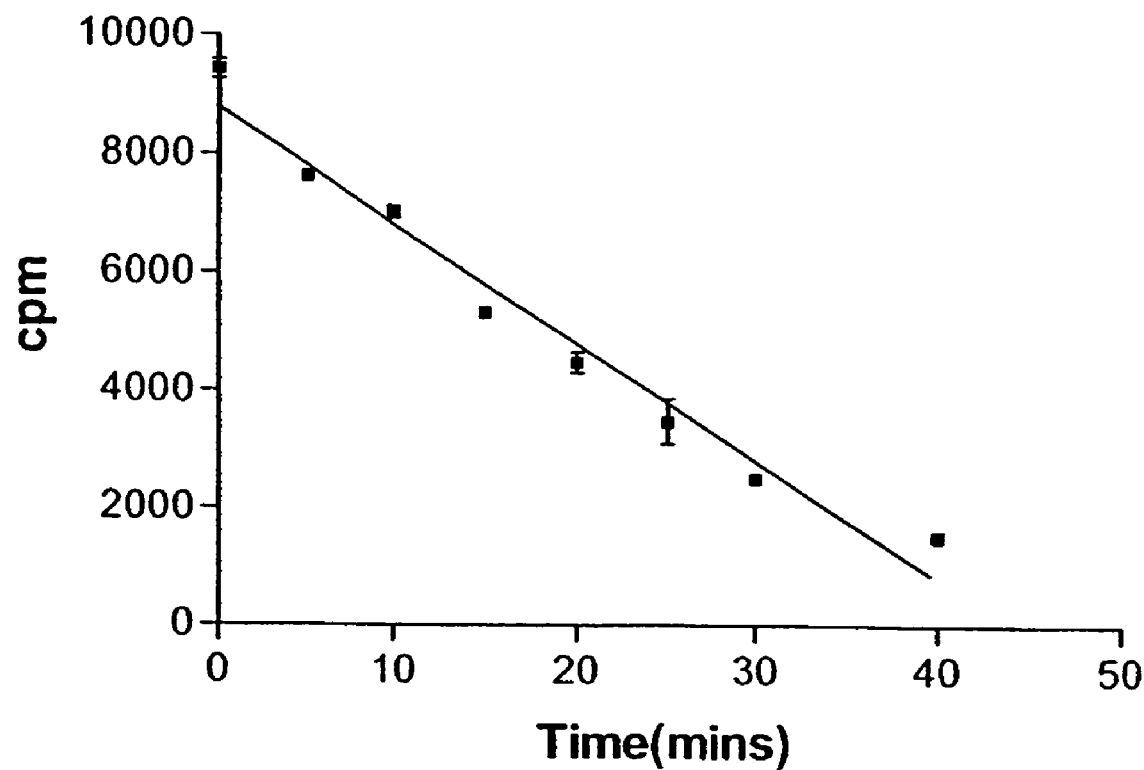
Figure 2 : Effect of incubation time on iNOS activity

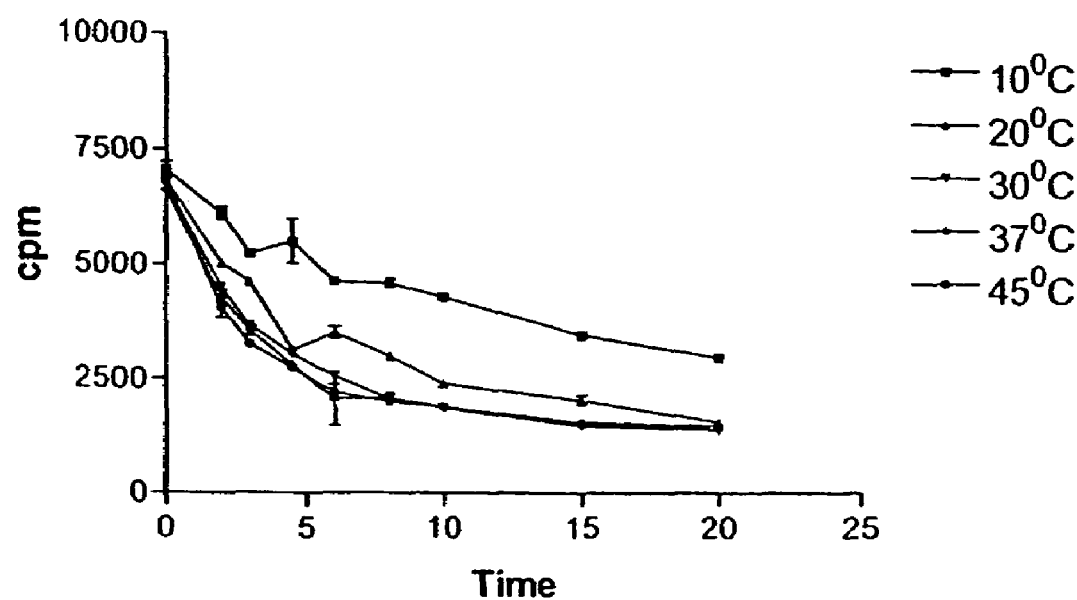
Figure 3 : Effect of temperature on iNOS activity

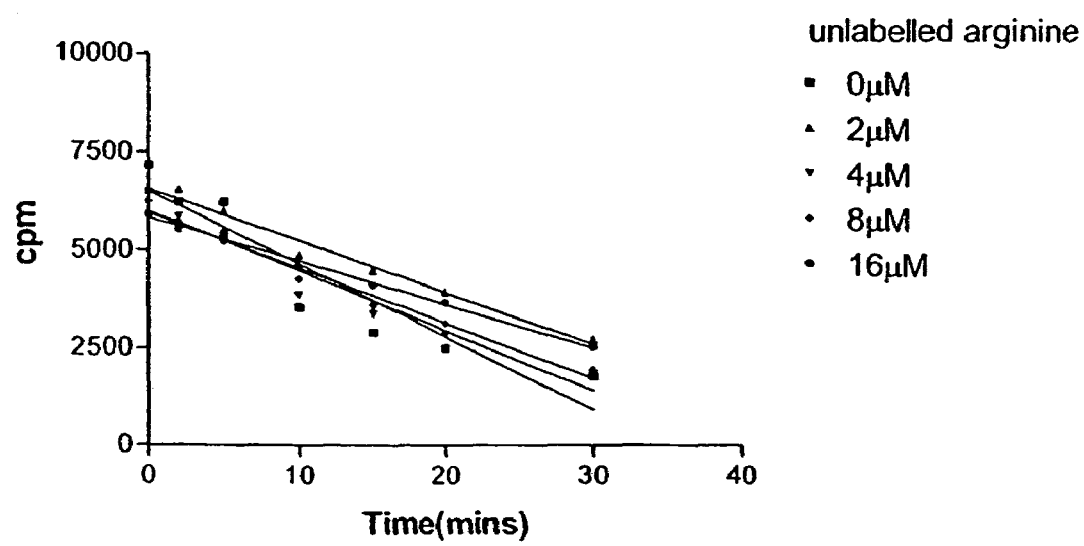
Figure 4: Effect of unlabelled arginine concentration on iNOS activity at 100,000 cpm

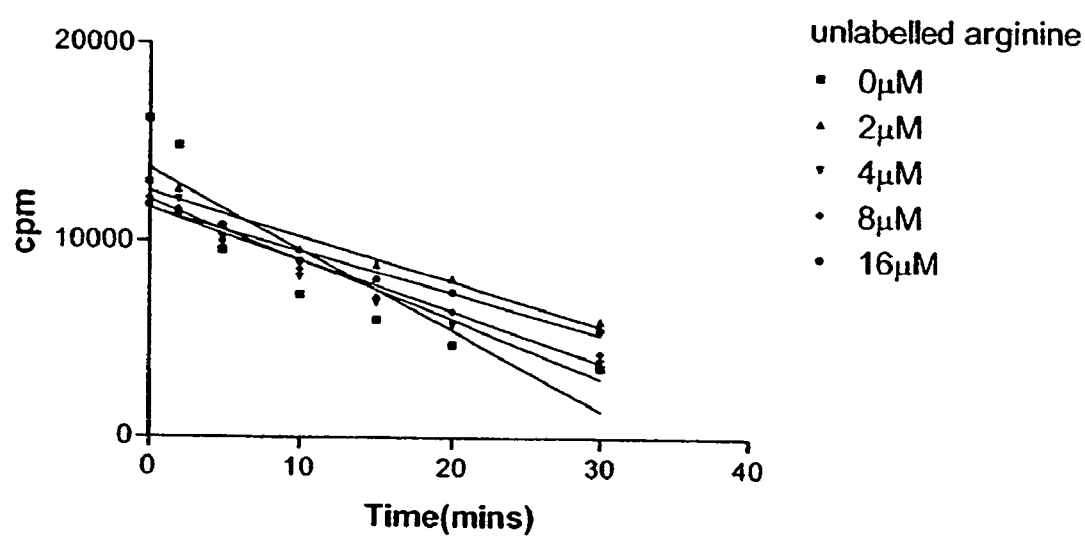
Figure 5 : Effect of unlabelled arginine concentration on iNOS activity at 200,000 cpm

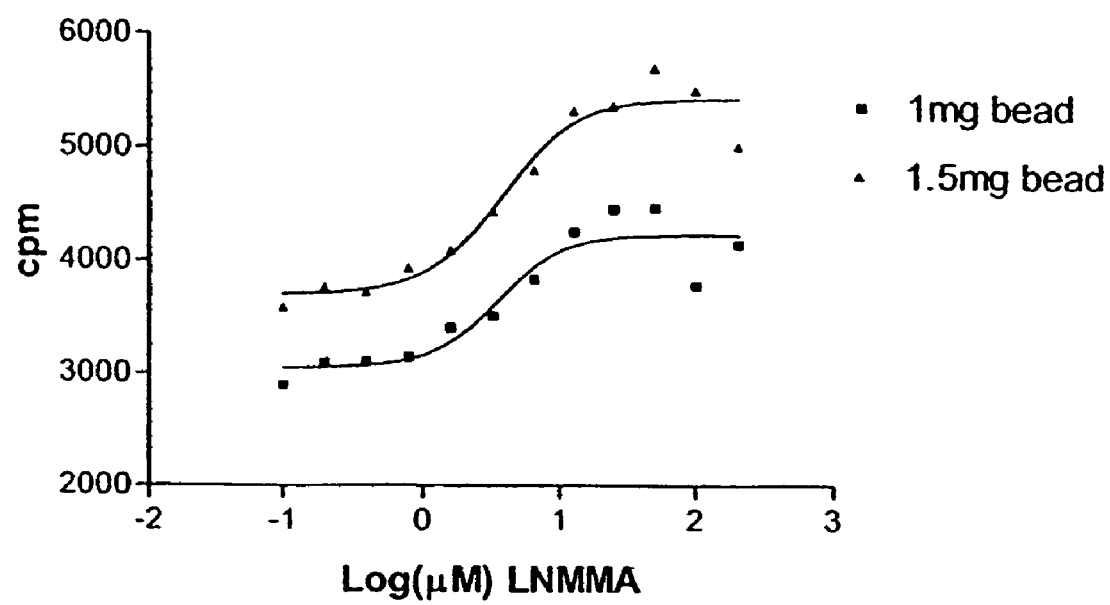
Figure 6 : Effect of bead concentration on iNOS activity

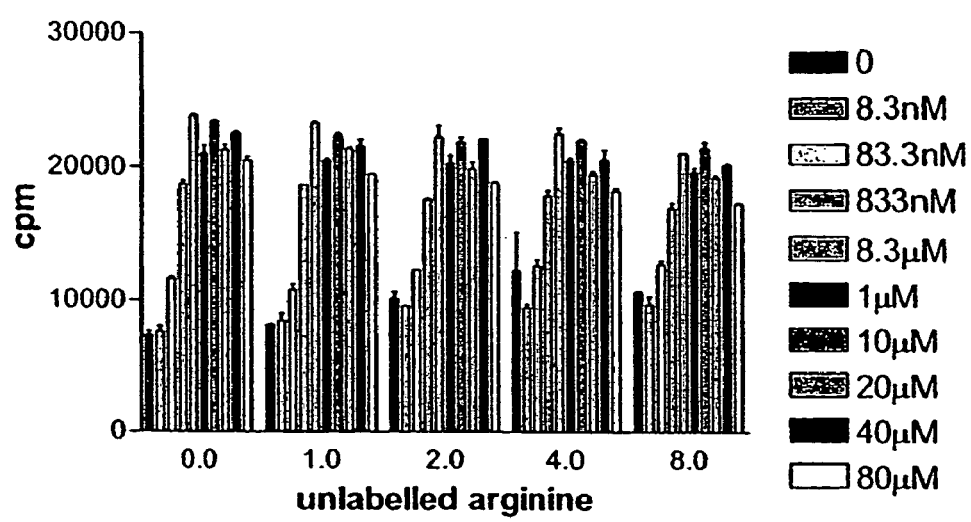
Figure 7 : Effect of unlabelled arginine concentration on iNOS response to SMT

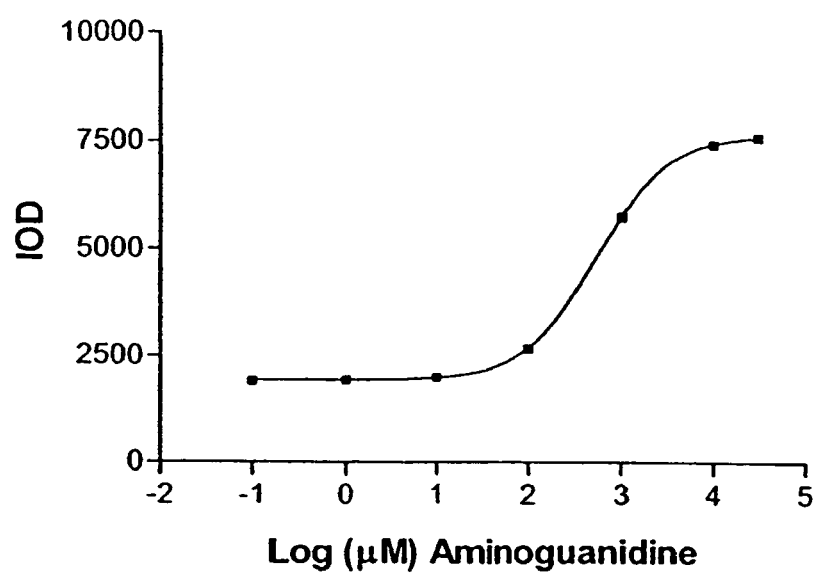
Figure 8: SPA Competition data using the NOS inhibitor aminoguanidine

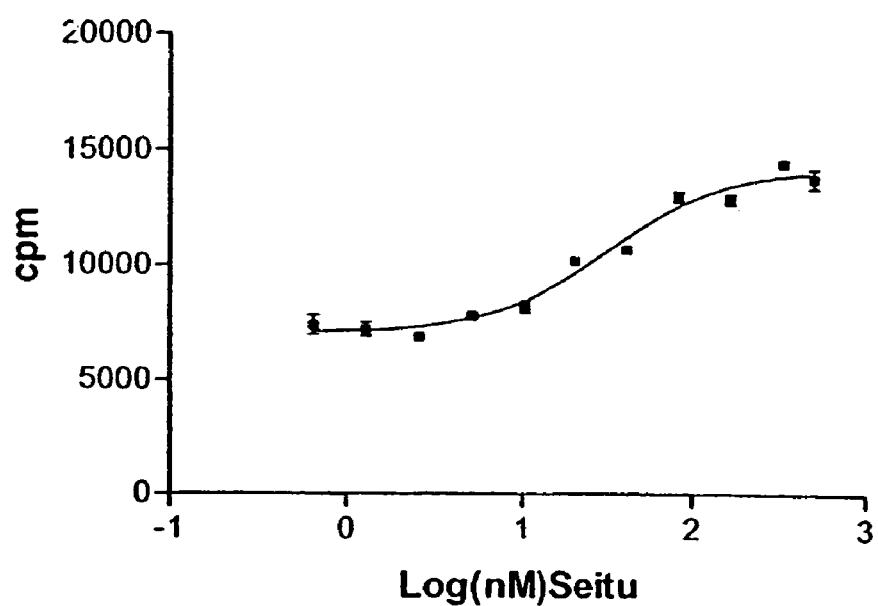
Figure 9: SPA Competition data using the NOS inhibitor 2-Ethyl-2-thiopseudourea hydrobromide (Seitu)

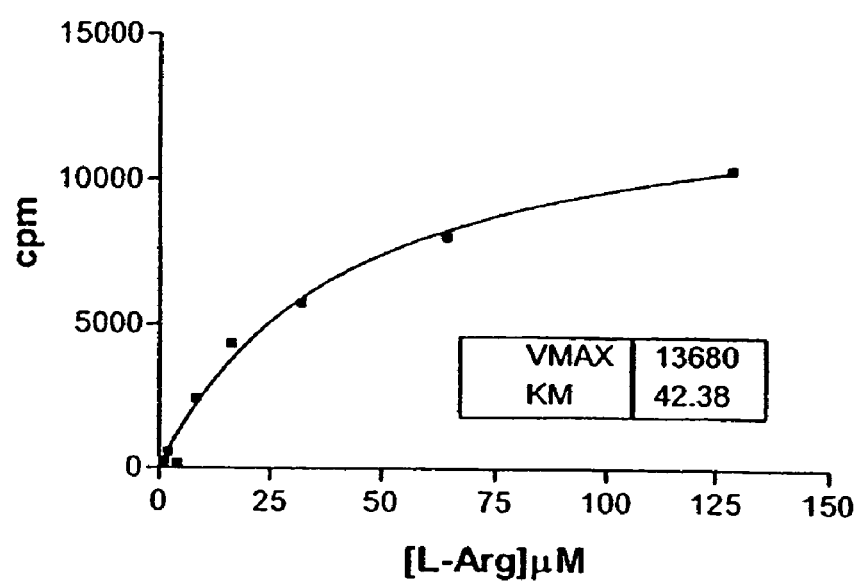
Figure 10 : Km analysis using iNOS scintillation proximity assay

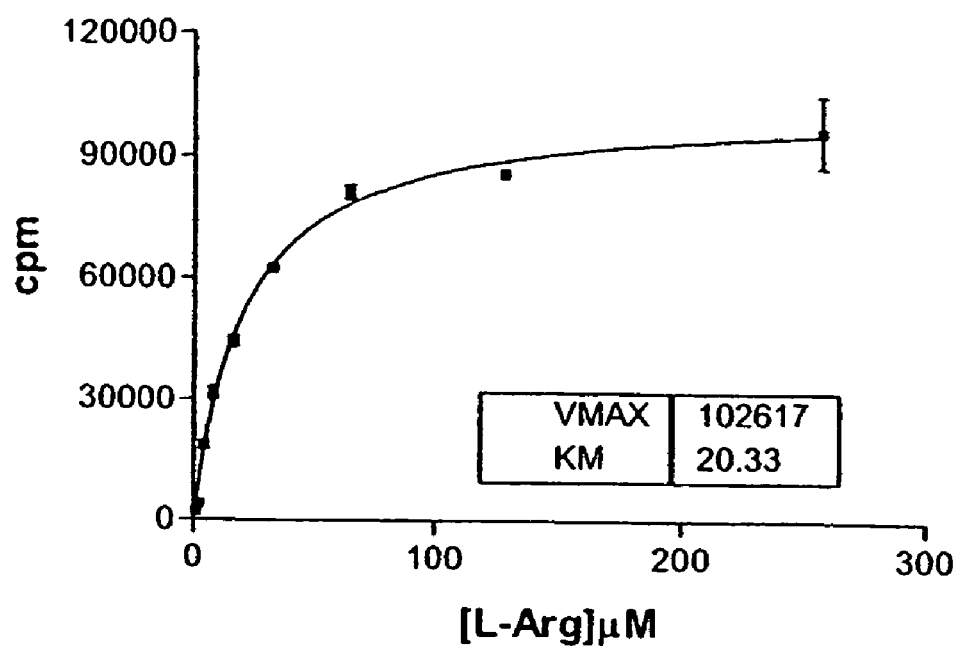
Figure 11 : Km analysis using Dowex ion exchange method

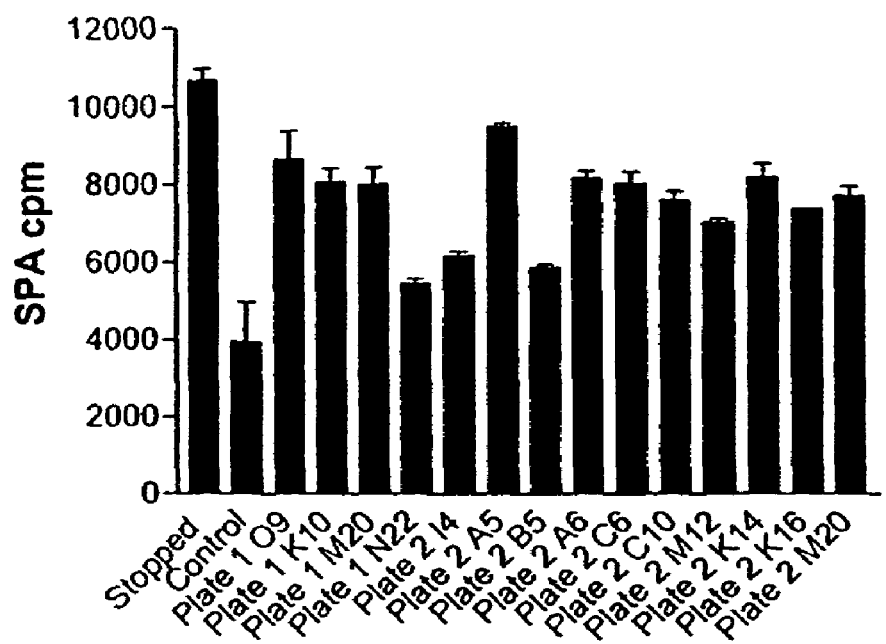
Figure 12 : LOPAC library screening results using iNOS SPA

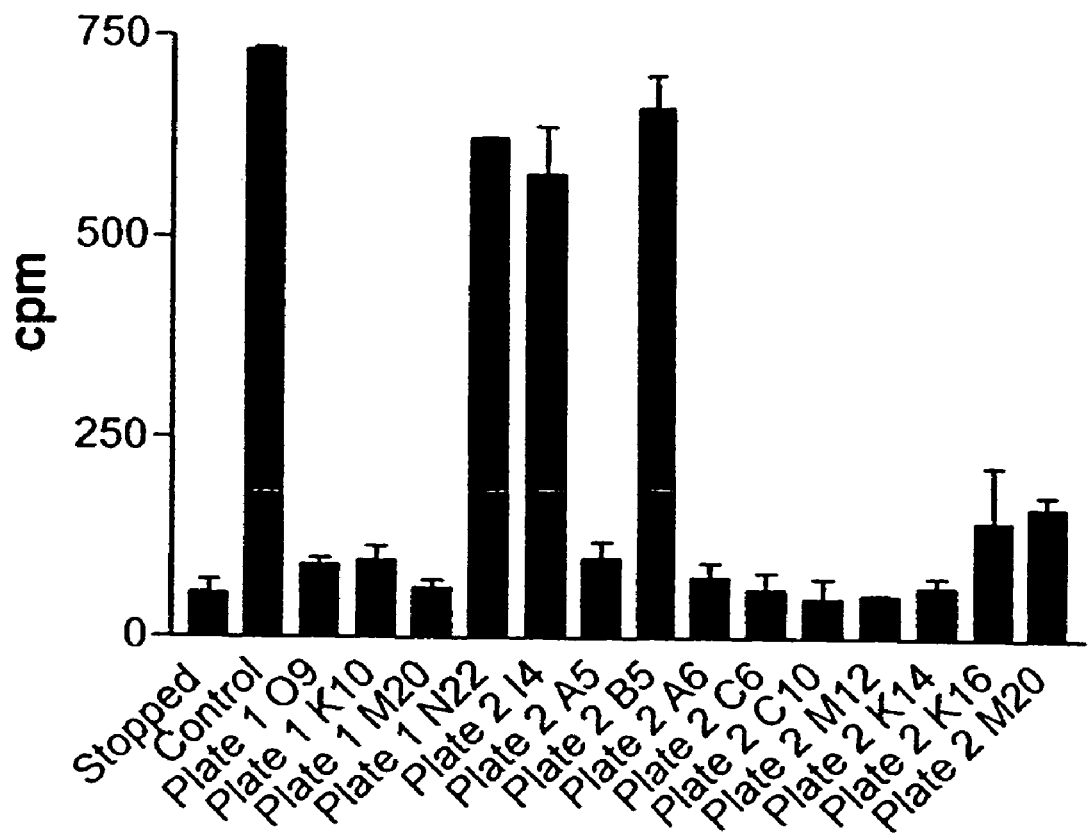
Figure 13 : LOPAC screening results using Dowex separation

NO SYNTHASE ASSAY PARTICLES AND METHOD

CROSS REFERENCE TO RELATED APPLICATIONS

This application is the US national phase under 35 U.S.C. of PCT application number PCT/GB02/01086 filed Mar. 11, 2002 which claims priority to Great Britain patent application number 0107563.9 filed Mar. 27, 2001.

The present invention relates to particles for use in a scintillation proximity assay. In particular, the invention relates to particles for use in a scintillation proximity assay for detecting NO synthase activity in a sample and methods using these particles for determining NO synthase activity or for detecting the presence of inhibitors or enhancers of NO synthase activity in a sample.

Nitric oxide (NO) is a major signalling molecule in neurons and the immune system, either acting within the cell or by penetrating cell membranes to affect adjacent cells (Cell 1994, 78, 919). It forms an important therapeutic target because it participates in a variety of physiological processes. As a result, it has stimulated intense and extensive research involving many scientific disciplines. Inhibitors of NO are under investigation for combatting shock, inflammation, stroke, and diabetes, while NO donors or precursors (e.g., L-arginine) are proving useful for treatment of vascular disease, hypertension, vasospastic disease, GI and urogenital problems, pulmonary hypertension, and bronchial asthma. (Ariggard E. Lancet.1994; 343: 1199-1206). NO has also been implicated in Parkinsons (Nat Med 1996; 2(9); 1017-21) and Alzheimers diseases, (Soc Neurosci Abstr 1995; 21:1010).

NO is formed by the oxidation of arginine via an intermediate, $L-N^G$-hydroxyarginine to form citrulline and nicotinamide adenine dinucleotide phosphate (NADP) in a reaction catalyzed by the enzyme nitric oxide synthase (NO synthase). The reaction requires several co-factors such as flavin adenine dinucleotide (FAD), nicotinamide adenine dinucleotide phosphate (reduced form) (NADPH), flavin mononucleotide (FMN) and biopterin (Reutov et al. Biochemistry (Moscow) 1998:63,(7);874-1029). In view of the importance of NO, NO synthase has long been recognised as a possible drug target.

Current methods for measuring NO synthase activity involve separating the substrate and products of the reaction using chromatographic techniques such as cation exchange HPLC/Dowex columns (Knowles and Salter, Methods in Molecular Biology, Vol 100, Nitric acid protocols, ed M. A. Titheradge), or thin layer chromatography using cellulose or silica gel and measuring their relative amounts. Other methods are available that are assay based and use radiolabelled arginine but these assays also involve a separation step.

Alternative techniques measure NO indirectly. For example, under physiological conditions NO is oxidised to nitrite and nitrates. The formation of nitrites can be detected in a colorimetric analysis as they react with a Griess reagent to form a purple azo derivative which can be monitored by its absorbance at 538 nm (Proc. Natl. Acad. Sci. USA 1987, 84, 9265). Similarly, the formation of nitrates may be quantified by reduction to nitrites using nitrate reductase prior to reaction with a Griess reagent.

Recent developments in genomics and combinatorial chemistry have generated large numbers of new drug targets and new compounds. In consequence, advances in drug discovery have focused on high throughput screening (HTS) technologies and miniaturisation. These technologies aim to screen large numbers (Typically, pharmaceutical companies each perform approximately 20 high throughput screens per year using between 200,000 and 2 million chemical entities) of either candidate drug targets or new compounds to uncover new leads in a short time (High-throughput screening for drug discovery, James R. Broach and Jeremy Thorner. Nature Vol. 384, Supp, 7 Nov. 1996, 1416.). Key to the success of such HTS techniques is the development of assays which can be adapted into a miniaturised format and which have only a minimum number of steps in order to reduce error and facilitate an automated screening process.

The current multi-step procedures for measuring NO synthase activity, especially those involving chromatography columns, would be difficult to automate and inconvenient to perform on a large number of samples simultaneously. Accordingly, to date, no HTS techniques have been made available for screening for NO synthase activity or for compounds which may act as enhancers or inhibitors of this activity.

Recently, assays based on homogeneous techniques have been developed and these are readily adaptable to HTS. These can involve detection via a solid phase binding step. One example has been the introduction of homogeneous radioimmunoassay technology, notably the technique of scintillation proximity assays (SPA) covered by U.S. Pat. No. 4,568,649. Scintillation proximity assay is a radioisotopic assay technique which has gained wide acceptance in recent years, and is applicable to radio-ligand binding assays, protein binding assays and enzyme assays. The technique relies on the observation that β-particles emitted from radioisotopes will travel only a limited distance in an aqueous environment (in the case of tritium β-particles, this is approximately 1.5 μm), before the energy is dissipated. SPA has been applied, for example, to receptor binding assays in which the scintillant particle, i.e. a polystyrene PVT-containing organic scintillant material or phosphor particle, is coated with a capture moiety, such as a receptor protein or a binding protein such as protein A. A sample, containing or suspected of containing a compound to be tested, is incubated in the presence of the scintillant particles together with a quantity of a radiolabelled ligand. Binding of the ligand to its receptor brings the radioisotopically-labelled molecule into close proximity with the microsphere causing β-particle energy to be transferred effectively to the scintillant, thereby causing the emission of light. Labelled molecules that remain free in solution are undetected because they are too distant from the solid phase. The assay therefore requires no separation step and the protocol has fewer pipetting steps compared with conventional, i.e. separation-based, assays.

It has been shown that in SPA-based assays there is often an increase in assay precision and reproducibility compared with traditional separation-based assays. Another advantage lies in the potential for increased sample throughput and capability for automation (Cook, N. D., Drug Discovery Today (1996), 1, 287-294). The application of SPA is not restricted to particular analytes or to types of molecule and in principle the technique can be applied in place of traditional separation-based assays. SPA results can be read in 96 and 384 well plates using standard microplate scintillation counters or in 384 and higher well density plates using LEADseeker™ (Amersham Pharmacia Biotech) Homogeneous Imaging System, Imaging System, (Imaging Proximity Assays—The LEADseeker™ Homogeneous Imaging System, Fowler, A. et al, Genetic Engineering News, Volume 18, Number 21, Nov. 15, 1998) The LEADseeker™ system feature a CCD camera allowing imaging of high density microplates in a single pass.

The present invention provides a new type of bead that is particularly suited for an SPA-based technique for the determination of NO synthase activity. These beads and their use in such an assay provide a homogeneous system that requires no separation stages thus allowing high throughput screening of compound libraries for inhibitors or activators of NO synthase in primary screens for therapeutic targets for NO metabolism. As well as screening for 'hits', kinetic analysis may also be carried out.

The invention accordingly provides in a first aspect a bead for use in a scintillation proximity assay for binding labelled arginine preferentially to citrulline comprising a phosphor said phosphor comprising an inorganic host material doped with an activator and characterised in that said bead has a coating of silica nanoparticles.

Suitably said phosphor comprises, in particular yttrium silicate doped with cerium ions or yttrium oxide doped with europium. Other suitable particles include those useful for applications as described in PCT Application No. WO 99/09415. The phosphor preferably has an emission maximum in the range 500 nm to 900 nm and consists generally of an inorganic host material doped with an activator. Examples of host materials are yttrium silicate, yttrium oxide, yttrium oxysulphide, yttrium aluminium gallium oxide (YAG), yttrium aluminium garnet, sodium yttrium fluoride ($NaYF_4$), lanthanum fluoride, lanthanum oxysulphide, yttrium fluoride ($YF_3$), yttrium gallate, gadolinium fluoride ($GdF_3$), barium yttrium fluoride ($BaYF_5$ or $BaY_2F_8$), gadolinium oxysulphide, zinc silicate, zinc sulphide and yttrium vanadate. The activator is generally a lanthanide or actinide moiety, and is preferably selected from terbium, europium, erbium, thulium, holmium, dysprosium, samarium, ytterbium, lutecium, gadolinium, uranium and uranyl $UO_2$, generally in the form of +2 or +3 ions. Other suitable phosphors are organic chelates of lanthanide or actinide transition metals, such as an imido phosphorane, as disclosed in EP 556005.

U.S. Pat. No. 6,073,379 discloses a process for the preparation of microspheres which have utility in SPA. The process involves coating a microsphere of polymeric material which has one or more surfactants adsorbed on its surface with one or more layers of silica nanoparticles. The resulting microspheres can be further modified to enhance their magnetic properties and for use in a variety of biological applications.

U.S. Pat. No. 4,278,651 describes a solid support for supporting a receptor molecule for use in a ligand binding assays. The solid support comprises a water insoluble polymer which includes at least one functional group for linking with the receptor. The polymer may be linked to a suitable substrate consisting of a non-porous core (such as glass) which is covered with layers of silica, alumina or thoria microparticles which form an outer porous coating.

Examples of scintillation proximity assays for measuring nitric oxide synthase activity are known in the literature. These assays suffer from the common problem in SPA technology in that they require the surface immobilisation of one of the binding partners, such as a receptor protein. Thus both Alderton and Lowe (Methods in Enzymology, 1999, Vol 301, 114-125) and Alderton et al. (Biochem J., 1998, 332, 195-201) describe the use of SPA beads having an attached haem-binding domain of neuronal Nitric Oxide Synthase for substrate binding.

In one embodiment, said bead may be coated with a coating substance and has a further coating of silica nanoparticles. Suitable coating substances include polymeric species including proteins such as streptavidin or oligosaccharides such as dextrans or agarose.

In a second aspect of the invention there is provided a method for determining NO synthase activity in a sample comprising the steps of:

a) forming a mixture in a fluid medium said mixture comprising:
   a sample to be tested; and
   a radiolabelled substrate of NO synthase
b) incubating said mixture under conditions to promote NO synthase activity
c) incubating said mixture in the presence of a solid phase coated with silica nanoparticles under conditions to cause at least a portion of radiolabelled substrate to become associated with the solid phase and wherein said solid phase comprises a scintillant; and
d) detecting amount of binding of the radiolabelled substrate to the solid surface wherein a decrease in binding compared to a control lacking the NO synthase enzyme is indicative of NO synthase activity.

Preferably, the solid phase is a bead for use in a scintillation proximity assay characterised in that said bead has a coating of silica nanoparticles in accordance with the first aspect of the invention. In one embodiment, the bead is a bead or particle comprising a scintillant. In a particularly preferred embodiment the bead is a phosphor particle.

In an alternative embodiment, the solid phase may take the form of a surface in which the scintillant, such as a phosphor, is present as a coating, applied onto a pre-formed surface, or may be dispersed in or constitute or form part of the bead or surface. In this embodiment, the solid phase suitably comprises an organic polymer, for example plastic or polymeric materials such as polystyrene, polyvinyltoluene and polyacrylamide, and the scintillant, such as a phosphor, may be coated onto the surface, or integrated into the matrix, of the solid phase. The solid phase may be relatively large, for example the surface of an assay vessel, such as the base or wall of the wells of a microwell plate, preferably a Cytostar™ (Amersham Pharmacia Biotech) plate or Flashplate™ (NEN).

In a third aspect of the invention there is provided a method for detecting an inhibitor or enhancer of NO synthase activity in a sample comprising the steps of:

a) forming a mixture in a fluid medium said mixture comprising:
   a chemical compound to be tested for inhibition or activation of NO synthase
   a radiolabelled substrate of NO synthase; and
   NO synthase enzyme
b) incubating said mixture under conditions to promote NO synthase activity
c) incubating said mixture in the presence of a solid phase coated with silica nanoparticles under conditions to cause at least a portion of radiolabelled substrate to become associated with the solid phase and wherein said solid phase comprises a scintillant; and
d) detecting the amount of binding of the radiolabelled substrate to the solid surface and comparing the amount of binding to a control lacking the chemical compound.

If a chemical compound acts as an inhibitor, higher levels of binding of the radiolabelled substrate are detected compared to a sample containing an enzyme only.

The assay method according to either the second or third aspect of the present invention is preferably performed in the wells of a multiwell plate, eg. a microplate having 24, 96, 384 or higher densities of wells e.g. 864 or 1536 wells. In a typical assay, a sample containing the enzyme (and, possibly, a test compound) is mixed with a radiolabelled substrate and scintillant particles in a fluid medium. The mixture is then incubated under conditions to promote NO synthase activity causing conversion of the radiolabelled substrate. The radiolabelled substrate that is not converted to a product of NO synthase activity will bind to the beads and, thus, be in close enough proximity to the scintillant surface to allow the radiative energy emitted by the radiolabelled substrate to activate the scintillant and cause the scintillant to emit light.

As the solid surface binds the radiolabelled substrate preferentially to the product, the amount of radiolabelled substrate bound depends on the degree of NO synthase activity. The intensity of light produced is directly related to the amount of radiolabelled ligand bound and is therefore inversely proportional to the amount of NO synthase activity.

The radiolabelled substrate is preferably radiolabelled arginine. NO synthase activity converts arginine to citrulline. Suitably, the radiolabel is one which emits β-particles or Auger electrons having a mean free path of up to 150 μm in aqueous media. These include isotopes commonly used in biochemical and molecular biology applications such as $^3$H, $^{14}$C and $^{125}$I.

The assay test sample is generally in a aqueous liquid such as a buffer solution. Suitable buffers for use in the invention include 50 mM phosphate buffer pH 7.4, and other physiological saline solutions such as Krebs-Ringer, Hanks or Dulbecco media.

Suitable detection techniques depend on the nature of the scintillant particle; when beads such as YSi particles are used, the detection step may be performed by counting techniques (such as a liquid scintillation counter, or a luminometer). Phosphor beads such as Yox particles can be detected by means of a charge coupled device (CCD) imager (such as a scanning imager or an imager) to image all of the wells of a multiwell plate. The LEADseeker™ system features a CCD camera allowing imaging of high density microplates in single pass. This can be used for reading assays in radioactive, fluorescent and luminescent formats. Imaging is quantitative and fast, and instrumentation suitable for imaging applications can now simultaneously image the whole of a multiwell plate.

In a fourth aspect of the invention, there is provided a test kit for determination of NO synthase activity in a sample, the kit comprising an SPA bead according to the first aspect of the invention.

In one embodiment, the kit may additionally comprise a radiolabelled substrate such as radiolabelled arginine (e.g. $^3$H Arg or $^{14}$C Arg). In another embodiment, the kit may further comprise a buffer suitable for NO synthase activity.

SPECIFIC DESCRIPTION

For the purposes of clarity, certain embodiments of the present invention will now be described by way of example with reference to the following figures:

FIG. 1 shows the activity of iNOS enzymes from different sources.

FIG. 2 shows the effect of incubation time on iNOS activity.

FIG. 3 depicts the effect of temperature on iNOS activity.

FIG. 4 shows the effect of unlabelled arginine concentration on iNOS activity at 100,000 cpm.

FIG. 5 shows the effect of unlabelled arginine concentration on iNOS activity at 200,000 cpm.

FIG. 6 depicts the effect of bead concentration on iNOS activity.

FIG. 7 shows the effect of unlabelled arginine concentration on iNOS response to SMT.

FIG. 8 illustrates SPA Competition data using the NOS inhibitor aminoguanidine.

FIG. 9 illustrates SPA Competition data using the NOS inhibitor 2-Ethyl-2-thiopseudourea hydrobromide (Seitu).

FIG. 10 depicts Km analysis using iNOS scintillation proximity assay.

FIG. 11 depicts Km analysis using Dowex ion exchange method.

FIG. 12 shows LOPAC library screening results using iNOS SPA.

FIG. 13 shows LOPAC screening results using Dowex separation.

EXAMPLE 1

Coating of Particles with a Silica Surface.

10 g Yox (yttrium oxide:europium; a red light emitting LEADseeker™ proximity particle) or YSi (cerium-doped yttrium silicate; a blue light emitting SPA particle) were mixed in 29.4 ml ethanol+0.6 ml $H_2O$ in a 50 ml tube. 0.4 ml ammonia (35% wt in $H_2O$) was added followed by 1 ml of tetraethylorthosilicate. Tubes were sealed with Parafilm and rolled at ambient temperature for 5 hrs. A further 0.2 ml $H_2O$ and 1 ml tetraethylorthosilicate was added to each tube and the mixture incubated with rolling overnight at room temperature.

The beads were pelleted by centrifugation at 4800×g for 5 minutes and the supernatants discarded. 3 washes in $H_2O$ were performed prior to final resuspension of the beads in 50 ml $H_2O$ and stored +4° C.

EXAMPLE 2

Selective Capture of $^{14}$C-labelled Arginine in the Presence of $^{14}$C-labelled Citrulline Capture of $^{14}$C labelled arginine and $^{14}$C citrulline was determined using 384 well plates in a total volume of 50 μl. 50,000 cpm $^{14}$C arginine (APBiotech, CFB63, 300 mCi/mMol stock solution) or citrulline (NEN, NEC214, 57.8 mCi/mmol), made up in water, was added to reaction buffer which contained 50 mM Tris-HCl, pH 7.5, 1.0 mM NADPH, 2.9 mM DTT, 3.8 μM FMN, FAD, and biopterin. "Stop" reagent, EDTA/aminoguanidine, was added to a final concentration of 4 mM and 89 μM respectively. Bead (100 mg/ml in water) was added to give 0.1 mg/well.

Plates were incubated at room temperature. The plates were counted using TopCount™ (Packard) (YSi-SPA beads) or the LEADseeker™ Generation II instrument (Yox beads) depending on the phosphor particles used.

SPA Results

Plate counted using TopCount following overnight incubation at room temperature. The results are shown in Table 1

| Bead type | Bead mg | Reaction buffer | | | Reaction buffer + water (30 µl) | | |
|---|---|---|---|---|---|---|---|
| | | Arg | Cit | Relative capture efficiency | Arg | Cit | Relative capture efficiency |
| YSi/Si | 0.25 | 2414.0 | 435.0 | 5.5 | 3445.0 | 371.0 | 9.3 |
| Si | 0.5 | 4941.0 | 741.0 | 6.7 | 6671.0 | 555.0 | 12.0 |
| | 0.75 | 7346.0 | 1023.0 | 7.2 | 10279.0 | 815.0 | 12.6 |
| | 1.0 | 9450.0 | 1280.0 | 7.4 | 12704.0 | 1023.0 | 12.4 |

LEADseeker™ Results

Plates were imaged for 2 minutes with coincident averaging. Coincident averaging is a method for eliminating cosmic noise events from data and employs a number of images acquired using the same exposure. Pixels differing by a determined value from the corresponding pixels in other exposures are disregarded.

Whereas coincident averaging employs a number of images using the same exposure time to remove cosmic noise, quasi-coincident averaging (Q-coincident) employs unequal exposure times, one shorter than the actual data image to identify and remove cosmic noise. The shorter exposure is normally one tenth of the image exposure time, algorithms then correct for the reduced exposure time. 3×3 binning was used. Binning is a process of combining charged packets from adjacent pixels during CCD(charge coupled device) readout. 3×3 binning is generally used with 384 well plates and is the combination of an array of 9 pixels.

Plate imaged following overnight incubation. The results are shown in Table 2. These show that both the new particles prepared capture arginine selectively with respect to citrulline.

EXAMPLE 3

Enzyme Assay—Activity of iNOS from Different Sources

Experiments were conducted to determine variation between different iNOS enzymes supplied by Oxis Research (Catalogue Number 27513) and Cayman Chemical Company (Catalogue Numbers 60864 and 60862). Reactions were carried out using 10 µl of each enzyme equivalent to 0.038 units/well, in reaction buffer (50 mM Tris pH 7.5, containing 1.0 mM NADPH, 3.8 µM FMN, 3.8 µM FAD, 3.8 µM biopterin, 2.9 mM dithiothreitol), 2 µM L-arginine, and 100,000 cpm $^3$H arginine (diluted in reaction buffer). The plate (Costar 3705) was incubated at room temperature for 40 minutes and the reaction terminated at various time intervals by the addition of 20 µl arginine binding beads (50 mg/ml) in 'stop' buffer (50 mM NaOH). The results were read using the TopCount (1 minute per well).

FIG. 1 shows the results of this experiment, from which it can be seen that there is some variation between the activity of each enzyme.

EXAMPLE 4

Enzyme Assay—pH and Time Dependency

Development work was conducted to ascertain the effect of time and pH on the efficacy of the enzyme reaction. Reaction conditions and data measurement were as described in Example 3 above, using 10 µl of iNOS (Cayman Chemical Company, Catalogue Number 60864) enzyme equivalent to 0.038 units/well.

FIG. 2 shows the linear response of the assay to the duration of enzyme incubation.

The optimum pH of the enzyme was found to be pH 7.5 (results not shown).

EXAMPLE 5

Enzyme Assay—Effect of Temperature

Experiments were carried out to determine the optimum temperature for conducting the enzyme assay. Assay conditions and data collection were as described in Example 4 above, the assays being conducted at 10° C., 20° C., 30° C., 37° C. and 45° C.

The results are depicted in FIG. 3 from which it can be seen that temperature does not have a marked effect on enzyme activity at temperatures in the range of 20-45° C.

EXAMPLE 6

Enzyme Assay—Effect of Label Concentration

Experiments were conducted to determine the effect of label concentration on enzyme activity at a range of unlabelled arginine concentrations (0, 2, 4,8, 16 µM). Assay conditions and data collection were as essentially as described in Example 4 above, with assays being carried out using 100,000 cpm and 200,000 cpm $^3$H.

The results of these experiments can be seen in FIGS. 4 & 5. Good sensitivity was found using 100,000 cpm $^3$H and 2 µM unlabelled arginine.

EXAMPLE 7

Enzyme Assay—Effect of Bead Concentration

Studies to determine the effect of bead concentration were conducted using 1 mg bead/well or 1.5 mg bead/well (otherwise assay conditions are as described in Example 4 above). The effect of the known NOS inhibitor LNMMA ($N^G$-methyl-L-arginine (Sigma Aldrich Inc., Catalogue Number M-7033) was investigated, using the assay conditions described at Example 4 above.

The results indicate that although adding more beads increases the cpm obtained, the shape of the inhibition curves remains essentially unaltered (FIG. 6).

EXAMPLE 8

Enzyme Assay—Assay Volumes

Assay volumes up to 50 µl were investigated, using the method described at Example 4 above. Although the results are not shown, the data were variable. Similarly, results with less than or more than 20 µl of stop volumes were poor, optimum results being obtained with 20 µl of 50 mM NaOH.

EXAMPLE 9

Enzyme Assay—Effect of Solvents

The effect of using different solvents to dissolve test inhibitor compounds was tested, using the assay conditions as described in Example 4 above. The data from these experiments are shown in Tables 3a-c. As can be seen, both the nature and the concentration of the solvent used to dissolve the inhibitor can affect the results of the assay. Appropriate 'experimental controls' should therefore be used in all experiments.

TABLE 3a

| 1% | Time (mins) cpm | | | | Ratio Time | % change |
|---|---|---|---|---|---|---|
| Solvent | 0 | 5 | 10 | 20 | 0/20 mins | in ratio |
| water | 15697 | 8871 | 5255 | 2200 | 7.14 | — |
| methanol | 14914 | 8639 | 4989 | 1973 | 7.56 | — |
| ethanol | 13409 | 9004 | 5580 | 2040 | 6.57 | 8% |
| acetone | 12884 | 8509 | 5169 | 1971 | 6.54 | 8% |
| DMSO | 10324 | 7128 | 4330 | 1615 | 6.39 | 10% |

TABLE 3b

| 5% | Time (mins) cpm | | | | Ratio Time | % change |
|---|---|---|---|---|---|---|
| Solvent | 0 | 5 | 10 | 20 | 0/20 mins | in ratio |
| water | 13910 | 8992 | 5398 | 1944 | 7.15 | — |
| methanol | 15317 | 7939 | 5466 | 2147 | 7.13 | — |
| ethanol | 13248 | 7465 | 6596 | 3161 | 4.19 | 41% |
| acetone | 12431 | 8409 | 6708 | 2601 | 4.78 | 33% |
| DMSO | 8530 | 4166 | 4453 | 1665 | 5.12 | 28% |

TABLE 3c

| 10% | Time (mins) cpm | | | | Ratio Time | % change |
|---|---|---|---|---|---|---|
| Solvent | 0 | 5 | 10 | 20 | 0/20 mins | in ratio |
| water | 13203 | 7502 | 5240 | 1867 | 7.07 | — |
| methanol | 12488 | 6631 | 4698 | 1975 | 6.32 | 10% |
| ethanol | 12008 | 6316 | 5987 | 3715 | 3.23 | 54% |
| acetone | 10201 | 6255 | 6464 | 3193 | 3.19 | 55% |
| DMSO | 6630 | 3884 | 3666 | 2138 | 3.10 | 56% |

EXAMPLE 10

Enzyme Assays—Effect of Plate Type

Several different 384 well plates were tested for their effect upon the assay. Assays were conducted as described in Example 4 above using a variety of plate types. The plates tested were: Costar 3704 (tissue culture treated, solid bottom); Costar 3705 (untreated, solid bottom); Costar 3706 (untreated, clear bottom); Greiner 781075 (untreated, solid bottom) and Matrix (no catalogue number available, untreated, solid bottom).

No significant differences were seen in using these different plate types in results obtained from the assay.

EXAMPLE 11

Enzyme Assays—Concentration of Unlabelled Arginine

As the concentration of labelled arginine is relatively low (100 nM), the effect of various concentrations of unlabelled arginine was investigated, using the assay conditions describe in Example 4 above and including the NOS inhibitor SMT (S-methylisothiourea, Sigma Aldrich Inc. M-3127) at a range of concentrations from 0-80 μM.

As can be seen from FIG. 7, concentrations of unlabelled arginine in excess of 2 μM altered the sensitivity of the assay.

EXAMPLE 12

Enzyme Assay—Competition Experiment I

The preferential capture of arginine compared to citrulline can be utilised in a signal decrease assay. The assay is performed in a 3074 Costar 384 well plate Enzyme (iNOS murine macrophage, recombinant. Cayman catalogue no. 60864, 112 units/ml) is diluted 10 times in assay buffer (1.2 mM NADPH, 3.6 mM DTT, 4.8 uM FAD, 4.8 uM FMN, 4.8 uM biopterin in 50 mM TRIS pH 7.5. Diluted enzyme (10 μl) is incubated with 1.5 μl inhibitor/agonist dissolved in 100% DMSO along with 10 μl $^{14}$C arginine tracer (APBiotech, CFB63, 300 mCi/mMol stock solution diluted in assay buffer to 100,000-150,000 cpm in 10 μl) for 1 hour at room temperature, protected from light. 10 μl LEADseeker beads suspended in a "stop" solution (360 μM aminoguanidine, 20 mM EDTA, pH 8) to 100 mg/ml (i.e 10 μl=1 mg/well) are added and the mixture incubated at room temperature for at least 2 hours. Control reactions were carried out by replacing the inhibitor with 1.5 μl water. The results are read by counting in LEADseeker™ (binning at 2×2, Q coincidence and imaged for 5 mins).

FIG. 8 shows a dose response curve and demonstrates inhibition of enzyme activity by aminoguanidine. FIG. 8 shows the IC50 value for aminoguanidine (represented by 50% inhibition of the enzyme) as about 500 uM. The baseline was determined using 1.5 μl 1 mM aminoguanidine (final concentration 70 μM) and maximum response using 1.5 μl 30 mM aminoguanidine (final concentration).

EXAMPLE 13

Enzyme Assay—Competition Experiment II

Experiments were carried out investigate the effect of the known NOS inhibitor SEITU (2-ethyl-2-thiopseudourea hydrobromide). The assay conditions were as described in Example 4 above employing a range of inhibitor concentrations.

An $IC_{50}$ value of 32 nM (95% confidence limits) was obtained for SEITU based upon the graph shown in FIG. 9.

EXAMPLE 14

Enzyme Assay—$K_m$ Determination

Km analysis was conducted on the assay using the standard assay conditions described in Example 4 above. Km analysis was also carried out following Dowex AG-50X ion exchange chromatography (Knowles and Salter, Methods in Molecular Biology, Vol 100, Nitric Acid Protocols, ed M. A. Titheradge).

Results of these experiments are shown in FIGS. 10 & 11.

EXAMPLE 15

Enzyme Assay—Signal Stability

Stability of the SPA signal was assessed over a period of 190 hours. Plates can be read 2 hours after the addition of the stop solution. Thereafter, up to 16 hours post-addition of the stop solution, there is a slight increase in the signal. However, from 16 hours to 190 hours post-addition the signal remains fairly constant. Furthermore, the shape of the graph does not alter from 2 hours to 190 hours post-addition of stop solution.

EXAMPLE 16

Enzyme Assay—Screening Study

The LOPAC library from Sigma Aldrich Inc. (Product Code SC001) was screened for inhibitor activity. The library consists of 640 diverse chemicals, including some known NOS inhibitors. The methodology is described below.

The 8 plate LOPAC library (Sigma, Product Code SC001) was initially reformatted from eight 96-well microplates to two 384-well microplates. Stock compounds were diluted to 4 mg/ml with DMSO. On consolidating in 384-well format they were further diluted to 0.4 mg/ml, by the addition of extra DMSO.

For the screening experiment, 1 µl aliquots of each compound were transferred to each of two assay plates. Standard NOS assay components were then added using a Beckman Multimek 96 (0.038 U/well NOS enzyme, ~100,000 cpm [3H]L-arginine, in buffer). Reactions were incubated at room temperature for 20 minutes then terminated by the addition of a 'stop' buffer (50 mg/ml YSi beads suspended in 50 mM NaOH). Plates were incubated overnight at room temperature before counting (1 minute per well, Wallac MicroBeta Trilux).

The results were analyzed with the Activity Base database program. Hits were identified by taking an arbitrary cut off figure based on the cpm levels generated in control assay wells.

From this a total of 22 'hits' were identified from Plate One and 42 from Plate Two.

The top thirteen compounds (those giving the highest signal) were identified from this initial single point screen as potential hits as defined by the criteria outlined above. The thirteen compounds were retested, in triplicate, using the SPA format and again, in duplicate, using a Dowex resin (Bio-Rad, 731-6213) separation, rather than SPA beads to generate the signal. The assay conditions were identical in both secondary testing experiments (as outlined above). The resin was converted to its sodium form by washing with 1M NaOH, then neutralizing with water. Under these conditions, arginine will bind to the resin, but the assay product citrulline will not, thus inhibition of iNOS will generate reduced counts with this type of signal reporting.

Of the 13 hits identified in the screen, 8 were known inhibitors in the LOPAC library.

The results are shown in FIGS. 12 and 13.

The compounds identified as NOS inhibitors are listed in Table 4.

TABLE 4

| Assay Identification Code | Sigma Identification Code | Chemical Name |
| --- | --- | --- |
| O 09 | A-145 | 1-Allyl-3,7-dimethyl-8-p-sulfophenylxanthine |
| K 10 | P-124 | Prazobind |
| M 20 | A-9512 | L(-)-Norepinephrine bitartrate |
| A05 | A9950 | Aniracetam |
| A06 | U 111 | (−)-trans-(1S,2S)-U-50488 Hydrochloride |
| C06 | M9656 | H-8 dihydrochloride |
| C10 | N7505 | NADPH tetrasodium |
| I04 | A5006 | L-Arginine |
| K014 | N-115 | Naltrindole Hydrochloride |
| K016 | M5171 | S-methyl-L-thiocitrulline acetate |
| M012 | A9834 | (+/−)-AMT hydrochloride |
| M020 | N-161 | NPC-15437 dihydrochloride |
| B05 | C8759 | Carisoprodol |
| N022 | P-103 | S(−)-3PPP Hydrochloride |

The invention claimed is:

1. A bead for use in a scintillation proximity assay for preferentially binding labeled arginine compared to citrulline, said bead comprising a phosphor particle, said phosphor including an inorganic host material doped with an activator and said bead further comprising a water permeable coating of silica nanoparticles, whereby said bead preferentially binds labeled arginine compared to citrulline.

2. The bead of claim 1 wherein said phosphor includes yttrium silicate doped with cerium ions or yttrium oxide doped with europium.

3. A method for determining NO synthase activity in a sample comprising the steps of:
   a) forming a mixture in a fluid medium, said mixture including:
      a sample to be tested; and
      a radiolabeled arginine;
   b) incubating said mixture under conditions to promote NO synthase activity;
   c) incubating said mixture in the presence of the bead of claim 1 under conditions to cause at least a portion of radiolabeled arginine to become associated with the bead; and
   d) detecting an amount of direct binding of the radiolabeled arginine to the bead wherein a decrease in binding compared to a control lacking the NO synthase enzyme is indicative of NO synthase activity.

4. A method for detecting an inhibitor or enhancer of NO synthase activity in a sample comprising the steps of:
   a) forming a mixture in a fluid medium, said mixture including:
      a chemical compound to be tested for inhibition or activation of NO synthase;
      radiolabeled arginine; and
      NO synthase enzyme;
   b) incubating said mixture under conditions to promote NO synthase activity;
   c) incubating said mixture in the presence of the bead of claim 1 under conditions to cause at least a portion of radiolabeled arginine to become associated with the bead; and
   d) detecting an amount of direct binding of the radiolabeled arginine to the bead and comparing the amount of binding to a control lacking the chemical compound.

5. A test kit for determination of NO synthase activity in a sample comprising the SPA bead of claim 1.

6. A test kit for determination of NO synthase activity in a sample comprising the SPA bead of claim 2.

* * * * *